United States Patent
Lock et al.

(10) Patent No.: US 7,491,824 B2
(45) Date of Patent: Feb. 17, 2009

(54) METHOD FOR PREPARING TIOTROPIUM SALTS

(75) Inventors: Ralf Lock, Mainz (DE); Werner Belzer, St. Goar (DE); Rainer Hamm, Ingelheim (DE); Monika Hofmann, Mainz (DE)

(73) Assignee: Boehringer Ingelheim Pharma GmbH & Co., KG, Ingelheim (DE)

( * ) Notice: Subject to any disclaimer, the term of this patent is extended or adjusted under 35 U.S.C. 154(b) by 478 days.

(21) Appl. No.: 11/209,323

(22) Filed: Aug. 23, 2005

(65) Prior Publication Data

US 2006/0047120 A1    Mar. 2, 2006

(30) Foreign Application Priority Data

Aug. 26, 2004    (DE)    ......... 10 2004 041253

(51) Int. Cl.
C07D 491/08    (2006.01)
(52) U.S. Cl. ....................................... 546/89
(58) Field of Classification Search ............. None
See application file for complete search history.

(56) References Cited

U.S. PATENT DOCUMENTS 6,747,154 B2 *  6/2004  Brandenburg et al. ......... 546/91

FOREIGN PATENT DOCUMENTS

WO    WO 03/057694 A1    7/2003

OTHER PUBLICATIONS

Carballido, Montserrat, et al: Synthesis of Amino Carba Sugars and Conformationally Restricted Polyhydroxy y-Amino Acids from (-) Quinic Acid; Eur. J. Org. Chem., 2004, 3663-3668—XP-002374123.

* cited by examiner

*Primary Examiner*—Rita J Desai
(74) *Attorney, Agent, or Firm*—Michael P. Morris; Mary-Ellen M. Devlin; Wendy Petka

(57) ABSTRACT

The invention relates to a new process for preparing tiotropium salts of general formula 1 wherein $X^-$ may have the meanings given in the claims and in the specification.

6 Claims, No Drawings

METHOD FOR PREPARING TIOTROPIUM SALTS

The invention relates to a new method for preparing tiotropium salts of general formula 1

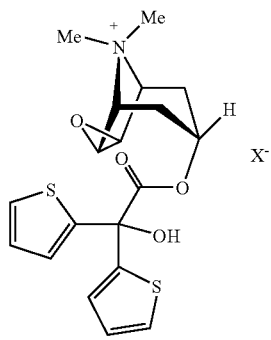

wherein $X^-$ may have the meanings given in the claims and in the specification.

BACKGROUND TO THE INVENTION

Anticholinergics may be used to advantage to treat a number of diseases. Particular mention may be made for example of the treatment of asthma or COPD (chronic obstructive pulmonary disease). Anticholinergics which have a scopine, tropenol or tropine basic structure are proposed for example by WO 02/03289 for the treatment of these diseases. Moreover, tiotropium bromide is particularly disclosed in the prior art as a highly potent anticholinergic. Tiotropium bromide is known for example from EP 418 716 A1.

In addition to the methods of synthesis for preparing scopine esters, disclosed in the prior art mentioned above, a process for preparing esters of scopine is disclosed particularly in WO03/057694.

The aim of the present invention is to provide an improved industrial method of synthesis which enables the compounds of general formula 1 to be synthesised more easily, in a manner which is an improvement on the prior art.

DETAILED DESCRIPTION OF THE INVENTION

The present invention relates to a process for preparing tiotropium salts of formula 1

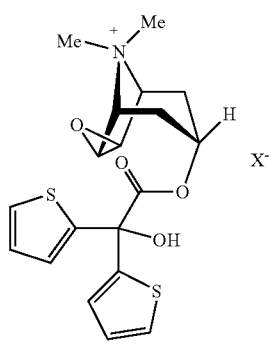

wherein
$X^-$ may represent an anion with a single negative charge, preferably an anion selected from among the chloride, bromide, iodide, methanesulphonate or trifluoromethanesulphonate, characterised in that a compound of formula 2

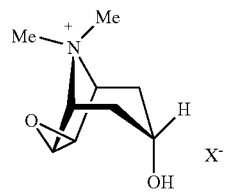

wherein $X^-$ may have the meanings given above, is reacted in one step with a compound of formula 3

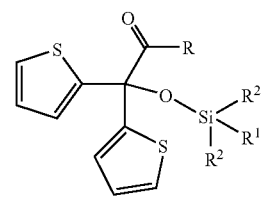

generated in situ, wherein
R is a group selected from among N-imidazolyl, N-triazolyl, —O—C(═NR')—NHR", —O—SO$_2$-phenyl, —O—SO$_2$-phenyl-methyl, —O—SO$_2$—R'—O—CO—C(methyl)$_3$, —O—CO-phenyl-NO$_2$, chlorine, bromine, —N$_3$ and —O—(P═O)R''', while
R' denotes $C_1$-$C_4$-alkyl or $C_3$-$C_6$-cycloalkyl;
R" denotes $C_1$-$C_4$-alkyl, $C_3$-$C_6$-cycloalkyl, $C_1$-$C_4$-alkylene-N($C_1$-$C_4$-alkyl)$_2$;
R''' denotes $C_1$-$C_4$-alkyl, —O—$C_1$-$C_4$-alkyl, phenyl or —O-phenyl
$R^1$ and $R^2$, which may be identical or different, may represent methyl, ethyl, propyl, butyl or phenyl, while phenyl may optionally be substituted by one or more $C_1$-$C_4$-alkyl groups, in a suitable solvent with the addition of a suitable base to yield a compound of formula 4

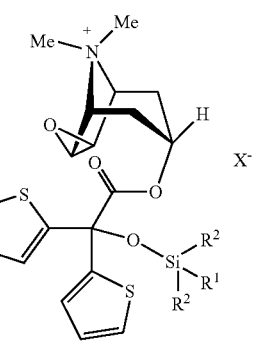

while the groups X⁻, R¹ and R² may have the meanings given above, and without being isolated the compound of formula 4 is converted into the compound of formula 1 by reaction with a suitable acid or a suitable desilylating reagent, cleaving the silyl group.

Preferably the present invention relates to a process for preparing tiotropium salts of formula 1, wherein X⁻ may represent an anion with a single negative charge selected from among chloride, bromide, iodide, methanesulphonate or trifluoromethanesulphonate, preferably chloride, bromide or methanesulphonate, particularly preferably bromide.

A process which is particularly preferred according to the invention is characterised in that the reaction is carried out with a compound of formula 3 generated in situ, wherein R is a group selected from among N-imidazolyl, N-triazolyl, —O—C(=NR')—NHR", —O—SO₂-phenyl-methyl, —O—CO—C(methyl)₃, and chlorine, while R' denotes methyl, ethyl or cyclohexyl;

R" denotes methyl, ethyl, cyclohexyl, C₂-C₃-alkylene-N(methyl)₂ or C₂-C₃-alkylene-N(ethyl)₂, and R¹ and R², which may be identical or different, represent methyl, ethyl, propyl or butyl.

A particularly preferred process according to the invention is characterised in that the reaction is carried out with a compound of formula 3 generated in situ, wherein R is a group selected from among N-imidazolyl, N-triazolyl, —O—C(=N-cyclohexyl)-NHcyclohexyl, —O—C(=N-ethyl)-NH—CH₂—CH₂—CH₂—NMe₂ and —O—CO—C(methyl)₃, preferably N-imidazolyl or N-triazolyl, particularly preferably N-imidazolyl and R¹ and R², which may be identical or different, represent methyl, ethyl, propyl or butyl, preferably methyl or ethyl, particularly preferably methyl;

R² denotes methyl or ethyl, preferably methyl.

The term alkyl groups, including those which are part of other groups, refers to branched and unbranched alkyl groups with 1 to 4 carbon atoms. Examples include: methyl, ethyl, propyl, butyl. Unless otherwise stated, the terms propyl and butyl used above include all the possible isomeric forms thereof. For example the term propyl includes the two isomeric groups n-propyl and iso-propyl, while the term butyl includes n-butyl, iso-butyl, sec. butyl and tert.-butyl.

The terms alkylene bridge or alkylene group, unless otherwise stated, refer to branched and unbranched alkyl groups with 1 to 4 carbon atoms, for example methylene, ethylene, propylene, butylene bridges. Particularly preferred are methylene, ethylene, propylene and butylene bridges. Unless otherwise stated, the terms ethylene, propylene, butylene used above include all the possible isomeric forms.

The terms phenyl-methyl and phenyl-NO₂ denote phenyl rings which are substituted by methyl or NO₂. All the possible isomers are included (ortho, meta or para), while para- or meta-substitution are of particular interest.

The term cycloalkyl groups refers to cycloalkyl groups with 3-6 carbon atoms, for example cyclopropyl, cyclobutyl, cyclopentyl or cyclohexyl.

This process may be carried out as described hereinafter. First of all, the compound of formula 3 is generated in situ in a suitable solvent. The phrase "in situ" indicates that the compound of formula 3 is prepared without then being isolated. The compound of formula 3 is prepared by reacting dithienylglycolic acid, preferably alkali metal salts of dithienylglycolic acid, particularly preferably sodium dithienylglycolate with a coupling reagent selected from among carbonyldiimidazole, carbonyldi-1,2,4-triazole, dicyclohexylcarbodiimide, ethyl-dimethylaminopropylcarbodiimide, toluenesulphonyl chloride, pivaloyl chloride, nitrobenzoic acid anhydride, oxalyl chloride, phosgene, sulphonyl chloride and phosphorus chlorides, preferably carbonyldiimidazole, carbonyldi-1,2,4-triazole, dicyclohexylcarbodiimide, ethyl-dimethylaminopropylcarbodiimide, particularly preferably carbonyldiimidazole in a suitable solvent, preferably in a polar, aprotic organic solvent, particularly preferably in a solvent selected from among acetonitrile, nitromethane, formamide, dimethylformamide, N-methylpyrrolidinone, dimethylsulphoxide, dimethylacetamide, tetrahydrofuran, dioxane and sulpholane, preferably tetrahydrofuran, dimethylformamide or N-methylpyrrolidone at a temperature of −20° C.-60° C., preferably −10° C.-45° C., particularly preferably −10° C.-25° C. and subsequently adding a silyl compound of formula 5

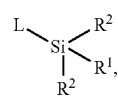

while the groups R¹ and R² may have the meanings given above and L denotes a leaving group which is preferably selected from among the halide, methanesulphonate, trifluoromethanesulphonate and para-toluenesulphonate, particularly preferably methanesulphonate, trifluoromethanesulphonate, bromine or chlorine, preferably also bromine or chlorine, while chlorine is of particular importance according to the invention.

The silyl compound 5 may either be added to the mixture of dithienylglycolic acid or dithienylglycolic acid salt with coupling reagent in the above-mentioned solvent, optionally in the presence of a base such as for example pyridine, imidazole or N-alkylamine, or first of all placed together with dithienylglycolic acid or the dithienylglycolic acid salt in the above-mentioned solvent, optionally in the presence of a base such as, for example, pyridine, imidazole or N-alkylamine, and then combined with the above-mentioned coupling reagent.

Preferably the three components mentioned above for forming the compound of formula 3 are added in stoichiometric amounts, but if desired the reaction may also be carried out with one of the three components present in excess (for example 1.1 to 1.5 equivalents). Preferably between 0.2 and 1.5 L, particularly preferably between 0.3 and 1 L of the specified solvent are used at this point per mol of the compound of formula 3 generated in situ.

After all three components have been added, the resulting solution is mixed at the temperature indicated above for about 5 minutes to 2 hours, preferably 10 minutes to 1 hour, particularly preferably for 20-40 minutes, for example by stirring, in order to form the compound of general formula 3.

The compound of formula 2 is then added to the solution thus obtained. This may be done either by the addition of a solution or suspension of the compound of formula 2 in one or more of the above-mentioned solvents or by, preferably batchwise, addition of the actual compound of formula 2. If the compound of formula 2 is added after being dissolved or suspended in one or more solvents, it is convenient to use the same solvent which is used for the preparation in situ of the compound of formula 3.

The amount in which the compound of formula 2 is added is determined by the amount of compound of formula 3 generated in situ. If the three components dithienylglycolic acid or dithienylglycolic acid salt, coupling reagent and compound of formula 5 are used in stoichiometric quantities to form the compound of formula 3, the compound of formula 3 is present in the molar amount which was selected for the three components dithienylglycolic acid or dithienylglycolic acid salt, coupling reagent and compound of formula 5. If the three components dithienylglycolic acid or dithienylglycolic acid salt, coupling reagent and compound of formula 5 are not used in stoichiometric amounts to form the compound of formula 3, the compound of formula 3 is present in the molar amount of the particular one of the three starting compounds dithienylglycolic acid or dithienylglycolic acid salt, coupling reagent and compound of formula 5 which is present in the smallest quantity.

The molar ratio of compound of formula 2 to compound of formula 3 generated in situ is preferably maintained within the range from 2:1 to 1:5, preferably 1.5:1 to 1:3, particularly preferably 1:1 to 1:2, while a ratio of 1:1 to 1:1.5 according to the invention is of particular importance.

After the addition of the compound of formula 3 the reaction mixture obtained is combined with a base taken up in a suitable solvent. Suitable solvents according to the invention are those mentioned hereinbefore. Preferably the solvent used here is the one which is also used to form the compound of formula 3. The bases used may be organic or inorganic bases. Organic bases used are preferably alkali metal imidazolides which may be generated in situ for example from the alkali metals and imidazole or the alkali metal hydrides and imidazole. Preferred alkali metal imidazolides include imidazolides of lithium, sodium or potassium, sodium or lithium imidazolide being preferred according to the invention. Particularly preferred are alkali metal alkoxides of sterically hindered alcohols (e.g. potassium tert.butoxide). Other preferred bases according to the invention are selected from among lithium diisopropylamide (LDA), lithium or sodium hexamethyldisilazane (LiHMDS or NaHMDS). Suitable inorganic bases preferably include hydrides of lithium, sodium or potassium. Sodium hydride is particularly preferably used as the inorganic base.

0.5-2 mol, particularly preferably 1-1.5 mol, of base are preferably added per mol of the compound of formula 2 used. Within the scope of the process according to the invention, however, it is generally sufficient if only 1-1.1 mol of base are added per mol of compound of formula 2 used.

To prepare the solution or suspension of base, between 0.2 and 1.5 L, particularly preferably between 0.3 and 1 L of the specified solvent are preferably used per mol of base.

The base is preferably added at a temperature of −20-60° C., preferably 0-45° C., particularly preferably 0-25° C. After the addition of the base the resulting mixture is stirred for about 10 minutes to 6 hours, preferably 30 minutes to 3 hours, particularly preferably 45 minutes to 1.5 hours at constant temperature in order to form the compound of formula 4.

In order to liberate the compound of formula 1 from the compound of formula 4 generated in situ, a suitable acid H—X is preferably added at a temperature below 10° C., particularly preferably at about 0° C. Preferably the choice of the acid depends on the anion $X^-$ in the desired end product of general formula 1. If desired, within the scope of the present invention, in addition to the acid H—X, a suitable desilylating reagent may also be added which is preferably selected from among the ammonium fluorides, particularly preferably tetrabutylammonium fluoride, tetraethylammonium fluoride, benzyltrimethylammonium fluoride, tetrahexylammonium fluoride, tetraoctylammonium fluoride or hydrogen fluoride, either free or complexed, such as e.g. pyridinium fluoride or triethylamine-HF complex.

As an alternative to using one of the above-mentioned acids the compound of formula 1 may also be liberated exclusively using the de-silylating reagents mentioned above.

Inasmuch as compounds of general formula 1 wherein $X^-$ denotes bromide are preferably synthesised within the scope of the present invention, the following procedure for preparing the tiotropium bromide which is preferred according to the invention is described. It is evident to the skilled man that, by a suitable choice of reagent H—X or Y—F [where Y may denote a cation such as a proton or a metal cation or ammonium, alkylammonium, tetraalkylammonium or pyridinium or a complex such as e.g. aluminium trifluoride-HF or some other fluoride donor such as e.g. diethylaminosulphur trifluoride (DAST)], a corresponding procedure can also be used analogously to prepare compounds wherein $X^-$ does not represent bromide.

In order to prepare compounds of formula 1 wherein $X^-$=bromide (=tiotropium bromide), preferably 0.2 to 20 mol, preferably 0.5 to 15 mol, particularly preferably 1 to 14 mol of hydrogen bromide, based on the compound of formula 2 used, are added at constant temperature. The hydrogen bromide used may be added either in gaseous form or in the form of preferably saturated solutions. Preferably, according to the invention, the hydrogen bromide is added after being dissolved in glacial acetic acid or water. Particularly preferably, a 33% hydrogen bromide solution in glacial acetic acid is used or particularly preferably it is used as an aqueous 62% hydrobromic acid. The acid is preferably added slowly enough that the temperature of the reaction mixture does not exceed 20° C. After the addition has ended the mixture is stirred at constant temperature, optionally also while cooling with ice (between 0.5 and 6 hours).

Working up may be carried out particularly as specified in the Examples, using methods known per se. For example, the reaction mixture is combined with a protic solvent, preferably with an alcohol, particularly preferably with methanol or ethanol or isopropanol. According to the invention, preferably 0.5 to 20 L, particularly preferably 0.7 to 13 L alcohol are added per mol of the compound of formula 2 used and the resulting mixture is stirred at a temperature of 0-60° C., preferably 10-45° C., particularly preferably 15-25° C. for a period of about 0.5-6 hours, preferably 0.5-5 hours, particularly preferably 0.5-4 hours.

Finally, the solution obtained is combined with a more non-polar organic solvent, preferably with a solvent selected from among a ketone (such as for example acetone or methylethylketone), an alcohol (such as for example methanol, ethanol, propanol, isopropanol, butanol or amylalcohol), toluene, ethyl acetate, n-butyl acetate, dichloromethane, diethyl ether, methyl-tert.-butyl-ether, tetrahydrofuran and dioxane, particularly preferably isopropanol, toluene or acetone.

After thorough mixing the product that crystallises out is separated off and washed with the above-mentioned solvent. In order to separate off any water-soluble impurities, the crude product may be treated with water or aqueous bromide solutions, e.g. sodium or potassium bromide solution.

A more extensive purification of the compounds of formula 1 thus obtained may be carried out, if necessary, by chromatography on silica gel or by recrystallisation from suitable solvents such as e.g. lower alcohols, for example methanol, ethanol or isopropanol, optionally with prior treatment with activated charcoal.

In view of its central importance as an intermediate in the process according to the invention for preparing the compounds of formula 1 the present invention further relates to the compound of formula 3

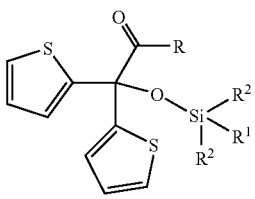

wherein R, $R^1$ and $R^2$ may have the meanings given above, per se.

In view of its central importance as an intermediate in the process according to the invention for preparing the compounds of formula 1 the present invention further relates to the compound of formula 4

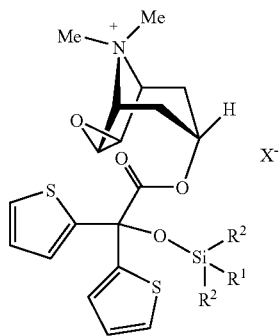

wherein $X^-$, $R^1$ and $R^2$ may have the meanings given above, per se.

The present invention also relates to the use of the above-mentioned compounds of formula 3 for preparing compounds of formula 1.

The present invention also relates to the use of the above-mentioned compounds of formula 4 for preparing compounds of formula 1.

The Examples that follow serves to illustrate some methods of synthesis carried out by way of example. They are to be construed only as possible methods described by way of example without restricting the invention to their contents.

SYNTHESIS EXAMPLE 1

5.43 g (50 mmol) chlorotrimethylsilane are added dropwise at 20° C. to a mixture of 13.1 g (50 mmol) sodium dithienylglycolate and 8.1 g (50 mmol) carbonyldiimidazole in 25 ml N-methylpyrrolidone (NMP).

After 30 min stirring 9.38 g (37.5 mmol) scopine methobromide are added and a solution of 2.59 g (38 mmol) imidazole and 1.52 g (38 mmol) sodium hydride (60%) in 15 ml NMP is added dropwise at 20° C. and the mixture is stirred for 1 h at 20° C.

After cooling to 0° C. 50 ml of a 33% solution of hydrogen bromide in glacial acetic acid are added dropwise while the temperature does not exceed 20° C. Then 50 ml methanol are added and the mixture is stirred for 1 h at 20° C. The reaction mixture is extracted twice with 200 ml toluene and, after separation of the toluene phase, crystallised from 150 ml isopropanol at 0° C. The crude product is filtered off, washed with 30 ml cold isopropanol and dried in vacuo.

Yield 15.0 g (85%, based on scopine methobromide).

SYNTHESIS EXAMPLE 2

5.43 g (50 mmol) chlorotrimethylsilane are added dropwise at 20° C. to a mixture of 13.1 g (50 mmol) sodium dithienylglycolate and 8.1 g (50 mmol) carbonyldiimidazole in 25 ml dimethylacetamide.

After 30 min stirring 9.38 g (37.5 mmol) scopine methobromide are added and a solution of 2.59 g (38 mmol) imidazole and 1.52 g (38 mmol) sodium hydride (60%) in 30 ml dimethylacetamide is added dropwise at 20° C. and the mixture is stirred for 1 h at 20° C.

After cooling to −4° C. 50 ml of a 33% solution of hydrogen bromide in glacial acetic acid are added dropwise while the temperature does not exceed 20° C. Then 50 ml methanol are added and the mixture is stirred for 3 h at 20° C. The reaction mixture is extracted with 500 ml toluene and, after separation of the toluene phase, crystallised from 150 ml isopropanol at 0° C. The crude product is filtered off, washed with 30 ml cold isopropanol and dried in vacuo.

Yield 14.1 g (80%, based on scopine methobromide).

SYNTHESIS EXAMPLE 3

5.43 g (50 mmol) chlorotrimethylsilane are added dropwise at 20° C. to a solution of 13.1 g (50 mmol) sodium dithienylglycolate and 8.1 g (50 mmol) carbonyldiimidazole in 25 ml dimethylformamide (DMF).

After 30 min stirring 12.5 g (50 mmol) scopine methobromide are added and a solution of 2.59 g (38 mmol) imidazole and 1.52 g (38 mmol) sodium hydride (60%) in 15 ml dimethylformamide is added dropwise at 20° C. and the mixture is stirred for 1 h at 20° C.

After cooling to −5° C. 50 ml of a 33% solution of hydrogen bromide in glacial acetic acid are added dropwise while the temperature does not exceed 20° C. Then 20 ml methanol are added and the mixture is stirred for 1 h at 20° C. The reaction mixture is extracted twice with 200 ml toluene and, after separation of the toluene phase, crystallised from 150 ml isopropanol at 5° C. The crude product is filtered off and recrystallised from 120 ml methanol with the addition of 5 g activated charcoal. After cooling to 0° C. the tiotropium bromide obtained is filtered off, washed with 5 ml cold methanol and dried in vacuo.

Yield 15.0 g (64% based on scopine methobromide).

SYNTHESIS EXAMPLE 4

5.43 g (50 mmol) chlorotrimethylsilane are added dropwise at 20° C. to a solution of 13.1 g (50 mmol) sodium dithienylglycolate and 8.1 g (50 mmol) carbonyldiimidazole in 25 ml dimethylformamide.

After 30 min stirring 12.5 g (50 mmol) scopine methobromide are added and a solution of 2.59 g (38 mmol) imidazole and 1.52 g (38 mmol) sodium hydride (60%) in 15 ml DMF at 20° C. is added dropwise and the mixture is stirred for 1 h at 20° C.

After cooling to −5° C. 50 ml of a 33% solution of hydrogen bromide in glacial acetic acid are added dropwise while the temperature does not exceed 20° C. Then 20 ml methanol are added and the mixture is stirred for 1 h at 20° C. The reaction mixture is extracted twice with 200 ml toluene and, after separation of the toluene phase, crystallised from 150 ml isopropanol at 5° C. The crude product is filtered off and recrystallised from 120 ml methanol with the addition of 5 g activated charcoal. After cooling to 0° C. the tiotropium bromide obtained is filtered off, washed with 5 ml cold methanol and dried in vacuo. The crystals thus obtained are dissolved in 20 ml water at 90° C. and the monohydrate of the tiotropium bromide is crystallised by cooling to 15° C. The product is filtered off, washed with 7 ml water and 8 ml acetone and dried by suction filtering.

Yield 9.8 g (40% based on scopine methobromide).

SYNTHESIS EXAMPLE 5

5.43 g (50 mmol) chlorotrimethylsilane are added dropwise at 20° C. to a mixture of 13.1 g (50 mmol) sodium dithienylglycolate and 8.1 g (50 mmol) carbonyldiimidazole in 25 ml dimethylformamide.

After 30 min stirring 12.5 g (50 mmol) scopine methobromide are added and a solution of 2.59 g (38 mmol) imidazole and 1.52 g (38 mmol) sodium hydride (60%) in 15 ml dimethylformamide is added dropwise at 20° C. and the mixture is stirred for 1 h at 20° C.

After cooling to 0° C. 5 ml of a 33% solution of hydrogen bromide in glacial acetic acid are added dropwise while the temperature does not exceed 20° C. Then 120 ml of 1M tetrabutylammonium fluoride in THF (0.12 mol) are added and the mixture is stirred for 1 h at ambient temperature. The reaction mixture is combined with 800 ml dichloromethane and stirred for 1 h at ambient temperature. The crystallised crude product is filtered off and recrystallised from 120 ml methanol with the addition of 5 g activated charcoal. After cooling to 0° C. the tiotropium bromide obtained is filtered off, washed with cold methanol and dried in vacuo.

Yield 9.5 g (44% based on scopine methobromide).

SYNTHESIS EXAMPLE 6

5.43 g (50 mmol) chlorotrimethylsilane are added dropwise at 20° C. to a solution of 13.1 g (50 mmol) sodium dithienylglycolate in 25 ml dimethylformamide. After 30 min stirring at ambient temperature 8.1 g (50 mmol) carbonyldiimidazole are added batchwise and the mixture is stirred for a further 10 min. Then 10 g (40 mmol) scopine methobromide are added and a solution of 2.59 g (38 mmol) imidazole and 1.52 g (38 mmol) sodium hydride (60%) in 15 ml dimethylformamide is added dropwise at 20° C. and the mixture is stirred for 1 h at 20° C.

After cooling to −5° C., 50 ml of a 33% solution of hydrogen bromide in glacial acetic acid are added dropwise, while the temperature does not exceed 20° C. Then 20 ml methanol are added and the mixture is stirred for 30 min at ambient temperature. The reaction mixture is extracted twice with 200 ml toluene and crystallised from 150 ml isopropanol by cooling to 5° C. The crystallised crude product is filtered off and recrystallised from 120 ml methanol with the addition of 5 g activated charcoal. After cooling to 0° C. the tiotropium bromide obtained is filtered off, washed with cold methanol and dried in vacuo. The product is dissolved in 24 ml water at 90° C. and the monohydrate of the tiotropium bromide is crystallised by cooling to 15° C. The product is filtered off and washed with 6.5 ml water and 10.5 ml acetone and dried.

Yield 8.1 g (42% based on scopine methobromide).

SYNTHESIS EXAMPLE 7

5.43 g (50 mmol) chlorotrimethylsilane are added dropwise at 20° C. to a solution of 13.1 g (50 mmol) sodium dithienylglycolate in 25 ml dimethylformamide. After 30 min stirring at ambient temperature 8.1 g (50 mmol) carbonyldiimidazole are added batchwise and the mixture is stirred for a further 10 min. Then 10 g (40 mmol) scopine methobromide are added and a solution of 2.59 g (38 mmol) imidazole and 1.52 g (38 mmol) sodium hydride (60%) in 15 ml dimethylformamide is added dropwise at 20° C. and the mixture is stirred for 1 h at 20° C.

After cooling to 10° C. 6 ml of a 33% solution of hydrogen bromide in glacial acetic acid are added dropwise while the temperature does not exceed 20° C. Then 120 ml tetrabutylammonium fluoride 1M in THF (0.12 mol) are added and the mixture is stirred for 30 min at ambient temperature. The reaction mixture is combined with 800 ml dichloromethane and stirred for 15 min at ambient temperature. The crystallised crude product is filtered off and recrystallised from 120 ml methanol with the addition of 2 g activated charcoal. After cooling to 0° C. the tiotropium bromide obtained is filtered off, washed with cold methanol and dried in vacuo. The product is dissolved in 18 ml water at 90° C. and the monohydrate of the tiotropium bromide is crystallised by cooling to 15° C. The product is filtered off and washed with 5 ml water and 8 ml acetone and dried.

Yield 6.5 g (34% based on scopine methobromide).

SYNTHESIS EXAMPLE 8

5.43 g (50 mmol) chlorotrimethylsilane are added dropwise at 20-30° C. to a solution of 13.1 g (50 mmol) sodium dithienylglycolate in 25 ml tetrahydrofuran.

After 60 min stirring 8.1 g (50 mmol) carbonyldiimidazole and after another 30 min 10.01 g (40 mmol) scopine methobromide are added and the mixture is stirred for a further 30 min. Then a solution of 2.60 g (38 mmol) imidazole and 1.65 g (38 mmol) sodium hydride (55%) in 25 ml dimethylformamide is added dropwise at 20° C. and the mixture is stirred for 1 h at 20° C.

After cooling to 0° C. 20 ml 62% hydrobromic acid are added dropwise while the temperature does not exceed 20° C. After 40 min stirring the reaction mixture is stirred into 350 ml isopropanol at 20° C. and cooled to 10° C. The crude product is filtered off, washed with 50 ml cold isopropanol and dried in vacuo.

Yield 18.9 g reddish-brown crystals, TLC corresponds to the comparison.

The crude product is dissolved in 100 ml methanol with 2.2 g activated charcoal at reflux temperature and filtered. Then the solution is evaporated down to 30 ml and cooled to 3° C. The crystals are filtered off, washed with 5 ml cold methanol and dried.

Yield 12.1 g whitish-beige crystals, TLC corresponds to the comparison.

The crystals thus obtained are dissolved in 28 ml water with 1.2 g activated charcoal at 80° C. and filtered. After cooling to 15° C. the tiotropium bromide monohydrate which has crystallised out is filtered off and dried.

Yield 9.4 g (48% based on the scopine methobromide used).

SYNTHESIS EXAMPLE 9

17.9 g (165 mmol) chlorotrimethylsilane are added dropwise at 0° C. to a solution of 39.3 g (150 mmol) sodium dithienylglycolate in 117 ml tetrahydrofuran.

After 60 min stirring at 10-20° C. the mixture is cooled to 0° C. and a solution of 24.3 g (150 mmol) carbonyldiimidazole in 105 ml dimethylformamide is added dropwise. After a further 30 min stirring 30.3 g (121 mmol) scopine methobromide are added and the mixture is stirred for a further 60 min at 10-20° C. It is cooled to 10° C. and a solution of 16.8 g (150 mmol) potassium tert. butoxide in 90 ml tetrahydrofuran is added dropwise at 10-20° C. and the mixture is stirred for 60 min at 20° C.

After cooling to 0° C. 60 ml 62% hydrobromic acid are added dropwise while the temperature does not exceed 20° C. After 40 min stirring the reaction mixture is stirred into 1150 ml isopropanol at 20° C. and cooled to 10° C. The crude product is filtered off, washed with 70 ml cold isopropanol and dried in vacuo.

Yield 61.5 g reddish-brown crystals, TLC corresponds to comparison.

The crude product is dissolved in 615 ml methanol with 6.15 g activated charcoal at reflux temperature and filtered. Then 570 ml methanol are distilled off and the solution is cooled to 10° C. The crystals are filtered off, washed with 35 ml cold methanol and dried.

Yield 40.9 g whitish-beige crystals, TLC corresponds to comparison.

The crystals thus obtained are dissolved in 94 ml water with 2.2 g activated charcoal at 80° C. and filtered, and then washed with 24 ml water. After cooling to 15° C. the tiotropium bromide monohydrate which has crystallised out is filtered off, washed with 25 ml water and 35 ml acetone and dried.

Yield 28.6 g (48% based on the scopine methobromide used).

The invention claimed is:

1. A process for preparing tiotropium salts of formula 1

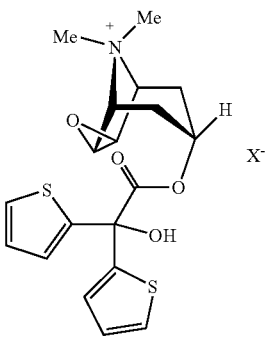

wherein
X$^-$ may represent an anion with a single negative charge, preferably an anion selected from among chloride, bromide, iodide, methanesulphonate or trifluoromethanesulphonate, wherein a compound of formula 2

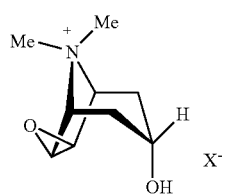

wherein X$^-$ may have the meanings given above, is reacted in one step with a compound of formula 3

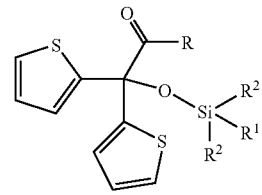

generated in situ
wherein
R is a group selected from N-imidazolyl, N-triazolyl, —O—C(=NR')—NHR", —O—SO$_2$-phenyl, —O—SO$_2$-phenyl-methyl, —O—SO$_2$—R'—O—CO—C(methyl)$_3$, —O—CO-phenyl-NO$_2$, chlorine, bromine, —N$_3$ and —O—(P=O)R''', where
R' denotes C$_1$-C$_4$-alkyl or C$_3$-C$_6$-cycloalkyl;
R" denotes C$_1$-C$_4$-alkyl, C$_3$-C$_6$-cycloalkyl, C$_1$-C$_4$-alkylene-N(C$_1$-C$_4$-alkyl)$_2$;
R''' denotes C$_1$-C$_4$-alkyl, —O—C$_1$-C$_4$-alkyl, phenyl or —O-phenyl;
R$^1$ and R$^2$, which may be identical or different, represent methyl, ethyl, propyl, butyl or phenyl, wherein phenyl may optionally be substituted by one or more C$_1$-C$_4$-alkyl groups, in a suitable solvent with the addition of a suitable base to yield a compound of formula 4

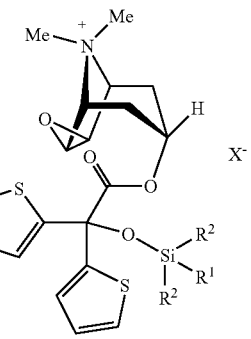

wherein the groups X$^-$, R$^1$ and R$^2$ may have the meanings as given above, and without being isolated the compound of formula 4 is converted into the compound of formula 1 by reaction with a suitable acid or a suitable desilylating reagent while cleaving the silyl group.

2. The process for preparing tiotropium salts of formula 1 according to claim 1, wherein
X$^-$ represents an anion with a single negative charge selected from chloride, bromide, iodide, methanesulphonate or trifluoromethanesulphonate.

3. The process for preparing tiotropium salts of formula 1 according to claim 1, wherein the reaction is carried out with a compound of formula 3 generated in situ, wherein
R is a group selected from among N-imidazolyl, N-triazolyl, —O—C(=NR')—NHR", —O—SO$_2$-phenyl-methyl, —O—CO—C(methyl)$_3$, and chlorine, where
R' denotes methyl, ethyl or cyclohexyl;
R" denotes methyl, ethyl, cyclohexyl, C$_2$-C$_3$-alkylene-N(methyl)$_2$ or C$_2$-C$_3$-alkylene-N(ethyl)$_2$, and
R$^1$ and R$^2$, which may be identical or different, denote methyl, ethyl, propyl or butyl.

4. The process for preparing tiotropium salts of formula 1 according to claim 1, wherein the reaction is carried out with a compound of formula 3 generated in situ, wherein R is a group selected from among N-imidazolyl, N-triazolyl, —O—C(=N-cyclohexyl)-NHcyclohexyl, —O—C(=N-ethyl)-NH—CH$_2$—CH$_2$—CH$_2$—NMe$_2$ and —O—CO—C(methyl)$_3$, preferably N-imidazolyl or N-triazolyl, particularly preferably N-imidazolyl and R$^1$ and R$^2$, which may be identical or different, denote methyl, ethyl, propyl or butyl, preferably methyl or ethyl, particularly preferably methyl;

R$^2$ denotes methyl or ethyl, preferably methyl.

5. The process for preparing tiotropium salts of formula 1 according to claim 1, wherein the compound of formula 3 is generated in situ in a suitable solvent by reacting dithienylglycolic acid or alkali metal salts of dithienylglycolic acid with a coupling reagent selected from among carbonyldiimidazole, carbonyldi-1,2,4-triazole, dicyclohexylcarbodiimide, ethyl-dimethylaminopropylcarbodiimide, toluenesulphonyl chloride, pivaloyl chloride, nitrobenzoic acid anhydride, oxalyl chloride, phosgene, sulphonyl chloride and phosphorus chlorides, and subsequently adding a silyl compound of formula 5

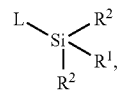

wherein the groups R$^1$ and R$^2$ may have the meanings given above and L denotes a leaving group which is selected from among the halide, methanesulphonate, trifluoromethanesulphonate and para-toluenesulphonate.

6. The process for preparing tiotropium salts of formula 1 according to claim 5, wherein the solvent is selected from acetonitrile, nitromethane, formamide, dimethylformamide, N-methylpyrrolidinone, dimethylsulphoxide, dimethylacetamide, tetrahydrofuran, dioxane and sulpholane.

* * * * *

UNITED STATES PATENT AND TRADEMARK OFFICE
CERTIFICATE OF CORRECTION

| | | |
|---|---|---|
| PATENT NO. | : 7,491,824 B2 | Page 1 of 1 |
| APPLICATION NO. | : 11/209323 | |
| DATED | : February 17, 2009 | |
| INVENTOR(S) | : Lock et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 656 days.

Signed and Sealed this
Fourth Day of October, 2011

David J. Kappos
*Director of the United States Patent and Trademark Office*